US00RE50630E

(19) United States
(12) Reissued Patent
Ruff

(10) Patent Number: US RE50,630 E
(45) **Date of Reissued Patent: *Oct. 14, 2025**

(54) USE OF AN ALL-D-PENTAPEPTIDE CHEMOKINE ANTAGONIST TO REDUCE OPIOID DOSE IN A PERSON WITH PAIN

(71) Applicant: Creative Bio-Peptides, Inc., Potomac, MD (US)

(72) Inventor: Michael R. Ruff, Potomac, MD (US)

(73) Assignee: Creative BioPeptides, Inc., Potomac, MD (US)

( * ) Notice: This patent is subject to a terminal disclaimer.

(21) Appl. No.: 17/698,065

(22) Filed: Mar. 18, 2022

Related U.S. Patent Documents

Reissue of:
(64) Patent No.: 10,624,945
Issued: Apr. 21, 2020
Appl. No.: 16/177,344
Filed: Oct. 31, 2018

U.S. Applications:
(60) Provisional application No. 62/579,545, filed on Oct. 31, 2017.

(51) Int. Cl.
*A61K 38/08* (2019.01)
*A61K 9/20* (2006.01)
*A61P 25/04* (2006.01)
*A61K 9/10* (2006.01)

(52) U.S. Cl.
CPC ..... *A61K 38/08* (2013.01); *A61P 25/04* (2018.01); *A61K 9/10* (2013.01); *A61K 9/20* (2013.01)

(58) Field of Classification Search
CPC ..... A61K 38/08; A61K 9/20; A61P 25/04
See application file for complete search history.

(56) References Cited

U.S. PATENT DOCUMENTS

| | | | | |
|---|---|---|---|---|
| 5,063,206 | A | 11/1991 | Bridge | |
| 5,276,016 | A | 1/1994 | Pert | |
| 5,514,670 | A | 5/1996 | Friedman | |
| 5,529,983 | A | 6/1996 | Pert | |
| 5,534,495 | A * | 7/1996 | Pert | A61K 38/162 514/17.7 |
| 5,567,682 | A | 10/1996 | Pert | |
| 5,739,109 | A | 4/1998 | Galpin | |
| 5,756,449 | A | 5/1998 | Andersen | |
| 5,834,429 | A | 11/1998 | Pert | |
| 5,863,718 | A | 1/1999 | Pert | |
| 6,011,014 | A * | 1/2000 | Andersen | A61K 38/08 514/17.9 |
| 6,242,564 | B1 | 6/2001 | Pert | |
| 6,265,374 | B1 | 7/2001 | Andersen | |
| 7,390,788 | B2 | 6/2008 | Pert | |
| 7,700,115 | B2 | 4/2010 | Ruff | |
| 8,772,231 | B2 | 7/2014 | Maggio | |
| 8,916,517 | B2 | 12/2014 | Coy | |
| 10,071,153 | B2 | 9/2018 | Ruff | |
| 10,130,674 | B2 * | 11/2018 | Pert | A61K 38/08 |
| 10,501,494 | B2 | 12/2019 | Ruff | |
| 11,510,961 | B2 * | 11/2022 | Ruff | A61K 38/08 |
| 2005/0013809 | A1 | 1/2005 | Owens | |
| 2011/0178013 | A1 | 7/2011 | Paternostre | |
| 2011/0245180 | A1 * | 10/2011 | Pert | A61P 25/16 514/17.7 |
| 2014/0322250 | A1 * | 10/2014 | Ruff | C07K 7/08 424/185.1 |
| 2014/0322251 | A1 * | 10/2014 | Ruff | C07K 7/08 424/185.1 |
| 2014/0322252 | A1 | 10/2014 | Ruff | |
| 2014/0323393 | A1 * | 10/2014 | Ruff | C07K 7/08 514/17.8 |
| 2017/0080019 | A1 | 3/2017 | Perricone | |
| 2017/0136095 | A1 | 5/2017 | Habener | |
| 2018/0344798 | A1 * | 12/2018 | Ruff | A61K 38/08 |
| 2018/0360907 | A1 * | 12/2018 | Ruff | A61K 38/08 |
| 2019/0022166 | A1 | 1/2019 | Ruff | |
| 2019/0125823 | A1 | 5/2019 | Ruff | |
| 2020/0246421 | A1 | 8/2020 | Lovejoy | |

(Continued)

FOREIGN PATENT DOCUMENTS

| | | | |
|---|---|---|---|
| CN | 101309680 | A | 11/2008 |
| CN | 101084002 | B | 1/2015 |
| JP | 11512732 | A | 11/1999 |

(Continued)

OTHER PUBLICATIONS

Lee et al., Neuropharmacology, 67:57-65, 2013.*
Ruff et al., CD4 receptor binding peptides that block HIV infectivity cause human monocyte chemotaxis. Relationship b vasoactive intestinal polypeptide. FEBS Lett, 1987, vol. 211, p. 17-22.
Abboud, et al., Inflammation Following Traumatic Brain Injury in Humans: Insights from Data-Driven and Mechanistic Models into Survival and Death. Front Pharmacol, 2016, vol. 7, 342.
Altman et al., Failure of vaccine test is setback in AIDS fight, New York Times, Sep. 22, 2007, 2 pages.
Amphetamines from www.DEA.gov, p. 1-4, Access Oct. 26, 2021 (2021).

(Continued)

*Primary Examiner* — Lora E Barnhart Driscoll
(74) *Attorney, Agent, or Firm* — Greenberg Traurig, LLP

(57) ABSTRACT

A method of treatment of pain in a person with a D peptide chemokine receptor antagonist (CRA), and a pharmaceutically acceptable carrier is disclosed. Because chemokines desensitize opiate receptors and enhance the perception of pain said D-peptide CRA, given with a suboptimal dose of an opioid, such as morphine, will restore opioid analgesic efficacy by blocking the cognate chemokine ligand from binding to its receptor and desensitizing the opioid receptor. This strategy of combining a suboptimal dose of morphine with a CRA enhances the potency of morphine, permitting use of lower doses of morphine to obtain equivalent and near maximal analgesia. Lower morphine (opioid) doses have less risk of adverse effects, and potentially also of development of tolerance and dependence.

9 Claims, 3 Drawing Sheets

Specification includes a Sequence Listing.

(56) References Cited

U.S. PATENT DOCUMENTS

| | | | |
|---|---|---|---|
| 2020/0377579 | A1 | 12/2020 | Penner |
| 2021/0187057 | A1 | 6/2021 | Ruff |

FOREIGN PATENT DOCUMENTS

| | | | |
|---|---|---|---|
| WO | 201084851 | | 7/2010 |
| WO | 2014047166 | A1 | 3/2014 |
| WO | 2017167934 | A1 | 10/2017 |
| WO | 2018087599 | A1 | 5/2018 |
| WO | 2018129200 | A2 | 7/2018 |
| WO | 2020018315 | A2 | 1/2020 |
| WO | 2022060424 | A1 | 3/2022 |
| WO | 2022192636 | A1 | 9/2022 |
| WO | 2022246233 | A1 | 11/2022 |

OTHER PUBLICATIONS

Arisi, et al., Increased CCL2, CCL3, CCL5, and IL-1β cytokine concentration in piriform cortex, hippocampus, and neocortex after pilocarpine-induced seizures. J Neuroinflammation, 2015, vol. 12, 129, p. 1-7.

Bamburg, et al., Actin dynamics and cofilin-actin rods in Alzheimer disease, Cytoskeleton, 2016, vol. 73, No. 9, p. 477-497.

Bamburg, et al., ADF/cofilin-actin rods in neurodegenerative diseases, Curr Alzheimer Res., 2010, vol. 7, No. 3, p. 241-250.

Barrett, et al., NOX2 deficiency alters macrophage phenotype through an IL-10/STAT3 dependent mechanism: implications for traumatic brain injury. J Neuroinflammation, 2017, vol. 14(65), p. 1-17.

Brenneman et al., Peptide T sequences prevent neuronal cell death produced by the envelope protein (gp120) of the human immunodeficiency virus. Drug Devel Res, 1988, vol. 15, p. 361-369.

Cai et al., Two different molecular mechanisms underlying progesterone neuroprotection against ischemic brain Damage. Neuropharmacology, 2008, vol. 55, p. 127-38.

Cerri, et al., The Chemokine CCL2 Mediates the Seizure-enhancing Effects of Systemic Inflammation. J Neurosci, 2016, vol. 36, p. 3777-3788.

Chen C, Zhang XR, Ju ZY, He WF., Advances in the research of cytokine storm mechanism induced by Corona Virus Disease 2019 and the corresponding immunotherapies, Chinese Journal of Burns. 2020; vol. 36(06), p. 471-475, E005, Epub Mar. 3, 2020.

Chen Y, Guo Y, Pan Y, Zhao ZJ. Structure analysis of the receptor binding of 2019-nCo V. Biochem Biophys Res Commun. 2020. Epub Feb. 23, 2020.

Cichon et al., Cofilin Aggregation Blocks Intracellular Trafficking and Induces Synaptic Loss in Hippocampal Neurons, Journal of Biological Chemistry, vol. 287, No. 6, p. 3919-2929, 2012.

Crews et al. Induction of innate immune genes in brain create the neurobiology of addiction. Brain, Behavior, and Immunity, 2011, vol. 25, Suppl 1, S4-S12. Epub Mar. 16, 2011.

Dhote et al., Prolonged inflammatory gene response following soman-induced seizures in mice. Toxicology, 2007, vol. 238, p. 166-176.

Di Prisco, et al., Functional adaptation of presynaptic chemokine receptors in EAE mouse central nervous system. Synapse, 2014, vol. 68, p. 529-535.

Di Prisco, et al., Rantes-mediated control of excitatory amino acid release in mouse spinal cord. J Neurochem, 2012, vol. 121, p. 428-437.

Dillman, et al., Gene expression profiling of rat hippocampus following exposure to the acetylcholinesterase inhibitor soman. Chem Res Toxicol 2009, vol. 22, p. 633-638.

Ensign, et al., Nanoparticle-based drug delivery to the vagina: A review. J Control Release, 2014, p. 500-514.

Fan, Y et al., MKEY, a Peptide Inhibitor of CXCL4-CCL5 Heterodimer Formation, Protects Against Stroke in Mice. Journal of the American Heart Association. Sep. 15, 2016, vol. 5, No. 9; pp. 1-8.

Feng, Z et al., Inspiration from the mirror: D-amino acid containing peptides in biomedical approaches. Biomolecular Concepts. Jun. 1, 2016, vol. 7, No. 3; pp. 179-187.

Flannery, et al., Persistent neuroinflammation and cognitive impairment in a rat model of acute diisopropylfluorophosphate intoxication. J Neuroinflammation 2016, vol. 13, No. 267, p. 1-16.

Funke, Sa et al., Peptides for Therapy and Diagnosis of Alzheimer's Disease. Current Pharmaceutical Design. 2012, vol. 18, No. 6; pp. 755-767.

Gibson et al., Feasibility of progesterone treatment for ischaemic stroke. J. Cerebral Blood Flow & Metabolism, 2016, vol. 36(3), p. 487-91.

Goodwin et al., "Peptides as therapeutics with enhanced bioactivity" Current Medicinal Chemistry 2012, vol. 19, p. 4451-4461.

Hayball, P. J. 1996. Chirality and nonsteroidal anti-inflammatory drugs. Drugs vol. 52 Suppl 5: p. 47-58.

He et al., Increased MCP-1 and microglia in various regions of the human alcoholic brain. Experimental Neurology, 2008, vol. 210(2), p. 349-58. Epub Jan. 15, 2008.

Heijo et al., Interactions Between Peptide and Preservatives: Effects on Peptide Self-Interactions and Antimicrobial Efficiency in Aqueous Multi-Dose Formulations, Pharm Res, 2015, vol. 32, p. 3201-3212.

Heseltine, et al., Randomized double-blind placebo-controlled trial of peptide T for HIV-associated cognitive Impairment. Arch Neurol, 1998, vol. 55, p. 41-51.

Hill et al., HIV envelope protein-induced neuronal damage and retardation of behavioral development in rat neonates. Brain Res, 1993, vol. 603(2), p. 222-33.

Huang et al., Clinical features of patients infected with 2019 novel coronavirus in Wuhan, China. Lancet. 2020, vol. 395, No. 10223, p. 497-506. Epub Jan. 28, 2020.

International Search Report for PCT/US19/40977 mailed Jan. 13, 2020.

Joy et al., CCR5 Is a Therapeutic Target for Recovery after Stroke and Traumatic Brain Injury. Cell, 2019, vol. 176(5), p. 1143-57 e13. Epub Feb. 23, 2019.

Kang et al., Cofilin, a Master Node Regulating Cytoskeletal Pathogenesis in Alzheimer's Disease, Journal of Alzheimer's Disease, 2019, vol. 72, S131-S144.

Kim et al., Chemokines and cocaine: CXCR4 receptor antagonist AMD3100 attenuates cocaine place preference and locomotor stimulation in rats. Brain, Behavior, and Immunity, 2017, vol. 62, p. 30-4. Epub Aug. 31, 2016.

Lee et al., Decreased pain responses of C-C chemokine receptor 5 knockout mice to chemical or inflammatory stimuli. Neuropharmacology, 2013, vol. 67, p. 57-65.

Li, et al., Effects of CC-chemokine receptor 5 on ROCK2 and p. MLC2 expression after focal cerebral ischaemia-reperfusion injury in rats. Brain Inj, 2016, vol. 30, p. 468-473.

Louboutin, et al., Role of CCR5 and its ligands in the control of vascular inflammation and leukocyte recruitment required for acute excitotoxic seizure induction and neural damage. FASEB J, 2011, vol. 25, p. 737-753.

Lusso et al., Cryptic Nature of a Conserved, CD4-Inducible V3 Loop Neutralization Epitope in the Native Envelope Glycoprotein Oligomer of CCR5-Restricted, but Not CXCR4-Using, Primary Human Immunodeficiency Virus Type 1 Strains. J Virol. 2005, vol. 79(11), p6957-68.

Mahalakshmi et al., The Use of D-Amino Acids in Peptide Design, New Frontier in Amino Acid and Protein Research, 2006, Chapter 5.9, p. 415-430.

Mao,et al., Exogenous administration of PACAP alleviates traumatic brain injury in rats through a mechanism Involving the TLR4/MyD88/NF-κB pathway. J Neurotrauma, 2012, vol. 29, p. 1941-1959.

Marastoni et al. Synthesis, metabolic stability and chemotactic activity of peptide T and its analogues. J Peptide Protein Res. 1990. vol. 35, p. 81-88.

Mayo Clinic (https ://www .mayoclinic.org/diseases-conditions/traumatic-brain-injury/diagnosis-treatment/drc-20378561, 2019.

(56) References Cited

OTHER PUBLICATIONS

Mehta et al., Across Speciality Collaboration UK. COVID-19: consider cytokine storm syndromes and immunosuppression. Lancet. 2020. Epub Mar. 13, 2020.
Melgarejo, et al., Monocyte chemoattractant protein-I: a key mediator in inflammatory processes. The International Journal of Biochemistry & Cell Biology. 2009; vol. 41(5): p. 998-1001. Epub Sep. 2, 2008.
Merck Manual (<https://www.merckmanuals.com/professional/neurologic-disorders/peripheral-nervous-system-and-motor-unit-disorders/amyotrophic-lateral sclerosis-als-and-other-motor-neuron-diseases-mnds> accessed on Sep. 17, 2021).
Moore et al. In vivo depression of lymphocyte traffic in sheep by VIP and HIV (AIDS)-related peptides. Immunopharmacology, 1988, vol. 16, p. 181-89.
Morganti, et al., Age exacerbates the CCR2/5-mediated neuroinflammatory response to traumatic brain injury. J Neuroinflammation 2016, vol. 13, p. 1-12.
Nayak et al., Chemokine CCR5 and cocaine interactions in the brain: Cocaine enhances mesolimbic CCR5 mRNA levels and produces place preference and locomotor activation that are reduced by a CCR5 antagonist. Brain, Behavior, and Immunity, 2020, vol. 83, 288-92. Epub Sep. 27, 2019.
NIH (<https://www.ninds.nih.gov/Disorders/All-Disorders/Encephalopathy-Information-Page> accessed Aug. 3, 2018).
Barbey-Morel C, McDonnell K, Ruff, MR, Pert C. A Peptide T Bolus Normalizes Growth Hormone Secretion Pattern in Two Children with AIDS. Peptides; 2002, vol. 6538, p. 1-3.
Bongiovanni, et al., Reduction of opioid reinforcement and physical dependence, inhibition of opioid-induced respiratory depression and normalization of opioid-induced dysregulation of mesolimbic chemokine receptors, Alcohol & Drug Abuse, 2022, vol. 238, p. 1-31.
Brenneman, D.E., Westbrook, G.L., Fitzgerald, S.P., Ennist, D.L., Elkins, K.L., Ruff, M.R. and Pert, C.B. Neuronal cell killing by the envelope protein of HIV and its prevention by vasoactive intestinal peptide. Nature, 1988, vol. 335, p. 639-642.
Brenneman, DE., Hauser, JM, Spong CY., Phillips, TM., Pert, CB., and Ruff, Mr. Vip and D-Ala1-Peptide T-amide release chemokines which prevent HIV-1 gp120 induced neuronal death. Brain Res., 1999, vol. 838, p. 27-36.
Bridge, T.P., Heseltine, P.N.R., Parker, E.S., Eaton, E., Ingraham, L.J., Gill, M., Ruff, M.R., Pert, C.B., and Goodwin, F.K. Improvements in AIDS patients on peptide T. The Lancet, 1989, p. 226-227.
Galvin Je et al., Clinical phenotype of Parkinson disease dementia, Neurology, 2006, vol. 67, No. 9, p. 1605-1611.
International Search Report and Written Opinion for PCT/US2019/037627, mailed Sep. 30, 2019.
International Search Report and Written Opinion for PCT/US2022/030305, mailed Sep. 13, 2022.
International Search Report and Written Opinion for PCT/US2022/032835, mailed Oct. 9, 2022.
Jellinger et al., Are dimentia with Lewy bodies and Parkinson's disease dementia he same disease?, BMC Medicine, 2018, vol. 16, No. 34, p. 1-16.
Libow LS et al., Parkinson's disease dementia: a diminshed role for the Lewy body, Parkinsonism Relat Disor., 2009, vol. 15, No. 8, p. 572-575.
Mulroney, S.E., K.J. McDonnell, C.B. Pert, M.R. Ruff, Z. Resch, W.K. Samson, and M.D. Lumpkin. HIV gp120 inhibits the somatotropic axis: a possible GH-releasing hormone receptor mechanism for the pathogenesis of AIDS wasting. Proc Natl Acad Sci USA, 1998, vol. 95, p. 1927-1932.
Noda, M, Daichi T, Ruff, MR and C. Pert. Neuropathic pain inhibitor, RAP-103, is a potent inhibitor of microglial CCL1/CCR8. Neurochem Int., 2017, vol. 119, p. 1-6.
Polianova, MT, Ruscetti FW, Pert CB, Leoung, G, Strang, S, Ruff, MR. Antiviral and immunological benefits in HIV patients receiving intranasal peptide T (DAPTA). Peptides, 2003, vol. 24, p. 1093-1098.
Pollicita M, Ruff MR, Pert CB, Polianova MT, Schols D, Ranazzi A, Perno CF, Aquaro S. Profound anti-HIV-1 activity of DAPTA in monocytes/macrophages and inhibition of CCR5-mediated apoptosis in neuronal cells. Antivir Chem Chemother, 2007, vol. 18, p. 285-95.
Ruff, et al., Potentiation of Morphine Antinociception and Inhibition of Diabetic Neuropathic Pain by the Multi-Chemokine Receptor Antagonist Peptide RAP-103, Life Science, 2022, vol. 306, p. 1-9.
Ruff, M.R., Smith, C., Kingan, T., Jaffe, H., Heseltine, P., Gill, M.A., Mayer, K., Pert, C.B., and Bridge, T.P. Pharmacokinetics of peptide T in patients with acquired immunodeficiency syndrome (AIDS). Prog Neuro Psychopharm., 1991, vol. 15, p. 791-801.
Ruff, Mr., Loyda M. Melendez-Guerrero., Quan-en Yang., Wen-Zhe Ho., Judy Mikovits, Candace B. Pert, and Francis Ruscetti. 2001. Peptide T inhibits HIV-1 infection mediated by the chemokine receptor-5 (CCR5). Antiviral Res., 2001, vol. 52, p. 63-75.
Schulz-Schaeffer, The synaptic pathology of α-synuclein aggregation in dementia with Lewy bodies, Parkinson's disease and Parkinson's disease dementia, Acta Neuropathol, 2010, vol. 120, p. 131-143.
Shaw et al., Peptide Regulation of Cofilin Activity in the CNAS: A Novel Therapeutic Approach for Treatment of Multiple Neurological Disorders, Pharmacology & Therapeutics, 2017, vol. 175, p. 17-27.
Wakabayashi et al., The Lewy body in Parkinson's disease: Molecules implicated in the formation and degradation of α-synuclein aggregates, Neuropathology, 2007, vol. 27, p. 494-506.
Owen et al., A theta-defensin composed exclusively of D-amino acids is active against HIV-1. J. Peptide Res, 2004, vol. 53, p. 469-76.
Padi et al., Attenuation of rodent neuropathic pain by an orally active peptide, RAP-103, which potently blocks CCR2- and CCR5-mediated monocyte chemotaxis and inflammation. Pain, 2012, vol. 153(1), p95-106. PubMed PMID: 22033364.
Paoletti, et al., Amygdalin analogues inhibit IFN-gamma signalling and reduce the inflammatory response in human epidermal keratinocytes. Inflammation, 2013, vol. 36, p. 1316-1326.
Peiris JS, Guan Y, Yuen KY. Severe acute respiratory syndrome. Nat Med. 2004; vol. 10(12 Suppl), S88-97. Epub Dec. 4, 2004.
Pert et al., Octapeptides deduced from the neuropeptide receptor-like pattern of antigen T 4 in brain potently inhibit human immunodeficiency virus receptor binding and T-cell infectivity. Proc Natl Acad Sci USA, 1986, vol. 83, p. 9254-9258.
Polianova et al., Chemokine receptor-5 {CCR5) is a receptor for the HIV entry inhibitor peptide T (DAPTA), Antiviral Res. 200, vol. 67, p. 83-92.
Polito, et al., Epithelia cells as regulators of airway inflammation. The Journal of Allergy and Clinical Immunology. 1998, vol. 102(5), p. 714-8. Epub Dec. 29, 1998.
Rachaudhuri S. P., E. M. Farber, and S. K. Raychaudhuri. 1999. Immunomodulatory effects of peptide T on Th 1/Th 2 cytokines. Int J Immunopharmacol, 1999, vol. 21, p. 609-15.
Ravizza, et al., Innate and adaptive immunity during epileptogenesis and spontaneous seizures: evidence from experimental models and human temporal lobe epilepsy. Neurobiol Dis, 2008, vol. 29, p. 142-160.
Rosi et al. Chemokine receptor 5 antagonist d -ALA-peptide T-amide reduces microglia and astrocyte activation within the hippocampus in a neuroinflammatory rat model of alzheimer's disease. Neuroscience, 2005, vol. 134, p. 671-676.
Ruan et al., Clinical predictors of mortality due to COVID-19 based on an analysis of data of 150 patients from Wuhan, China. Intensive Care Medicine. 2020. Epub Mar. 4, 2020.
Ruff et al., CD4 receptor binding peptides that block HIV infectivity cause human monocyte chemotaxis. Relationship o vasoactive intestinal polypeptide. FEBS Lett, 1987, vol. 211, p. 17-22.
Ruff et al., Peptide T[4-8] is Core HIV Envelope Sequence Required for CD4 Receptor Attachment, Lancet. 1987. vol. 330(8561), p. 751.
Ruff et al., Update on D-ala-peptide T-amide (DAPTA): a viral entry inhibitor that blocks CCR5 chemokine receptors. Curr HIV Res, 2003, vol. 1, p. 51-67.

(56) References Cited

OTHER PUBLICATIONS

Saez-Torres et al., Peptide T does not ameliorate experimental autoimmune encephalomyelitis (EAE) in Lewis rats, Clin. Exp. Lmmunol, 2000, vol. 121, p. 151-56.
Saika et al., CC-chemokine ligand 4/macrophage inflammatory protein-1beta participates in the induction of neuropathic pain after peripheral nerve injury. Eur J Pain, 2012, vol. 16, p. 1271-1280.
Saika et al., Chemokine CXCL1 is responsible for cocaine-induced reward in mice. Neuropsychopharmacology Reports. 2018, vol. 38(3), p. 145-8. Epub Sep. 4, 2018.
Servick, Unexpected drug emerges for stroke recovery. Science. Feb. 22, 2019. vol. 363(6429), p. 805.
Shen et al., . Postnatal activation of TLR4 in astrocytes promotes excitatory synaptogenesis in hippocampal neurons. J Cell Biol, 2016, vol. 215, p. 719-734.
Shi et al., COVID-19 infection: the perspectives on immune responses. Cell Death Differ. 2020. Epub Mar. 25, 2020.
Smith et al., Tritiated D-ala-peptide T binding: A pharmacologic basis for the design of drugs which inhibit HIV receptor binding. Drug Development Res, 1988, vol. 15, p. 371-379.
Song et al., "Effects of an Inhibitor of Monocyte Recruitment on Recovery from Traumatic Brain Injury in Mice Treated with Granulocyte Colony-Stimulating Factor," Int. J. Mol. Sci. Jul. 2, 2017; vol. 18(7), p. 1-16.
Song et al., Pharmacological Modulation of Functional Phenotypes of Microglia in Neurodegenerative Diseases. Front Aging Neurosci, 2017, vol. 9, p. 1-10.
Spisani et al. Chemotactic response of human monocytes to pentapeptide analog derived from immunodeficiency virus protein gp 120. Inflammation, 1990, vol. 14(1), p. 55-60.
Stewart et al., All-D-bradykinin and the problem of peptide antimetabolites. Nature, vol. 206, p. 619-620.
The Concussion Legacy Foundation (https://concussionfoundation . org/CTE-resources/what-is-CTE, 2019).
Thermo, N-Terminal Acetylation and C-Terminal Amidation of Peptides. Technical Information, 2004, 2 pages.
Trocello et al., Implication of CCR2 chemokine receptor in cocaine-induced sensitization. J Mol Neurosci. 2011, vol. 44(3), p. 147-51. Epub Mar. 23, 2011.
Uludag et al., IL-1β, IL-6 and IL1Ra levels in temporal lobe epilepsy. Seizure, vol. 26, p. 22-25.
Valekova et al., Revelation of the IFNα, IL-10, IL-8 and IL-1β as promising biomarkers reflecting immuno-pathological mechanisms in porcine Huntington's disease model. J Neuroimmunol, 2016 vol. 293, p. 71-81.
Vezzani et al., Brain inflammation as a biomarker in epilepsy. Biomark Med, 2011, vol. 5, p. 607-614.
Vezzani et al., The role of inflammation in epilepsy. Nat Rev Neurol, 2011, vol. 7, p. 31-40.
Victoria, et al. Knockdown of C-C chemokine receptor 5 (CCR5) is protective against cerebral ischemia and reperfusion injury. Curr Neurovasc Res, 2017, vol. 14, No. 2, pp. 125-131.
Villemagne et al., Peptide T and glucose metabolism in AIDS dementia complex. J Nucl Med, 1996, vol. 37, 1177-1180.
Vitaliti et al., Targeting inflammation as a therapeutic strategy for drug-resistant epilepsies: an update of new immune-modulating approaches. Hum Vaccin Immunother, 2014, vol. 10, 868-875.
Walsh et al., Amyloid-β and Proinflammatory Cytokines Utilize a Prion Protein-Dependent Pathway to Activate NADPH Oxidase and Induce Cofilin-Actin Rods in Hippocampal Neurons, PLOS One, 2014, vol. 9, Issue 4, e95995, p. 1-12.
Xu et al., Pathological findings of COVID-19 associated with acute respiratory distress syndrome. Lancet Respir Med. 2020. Epub Feb. 23, 2020.
Yoshikawa et al., Severe acute respiratory syndrome (SARS) coronavirus-induced lung epithelial cytokines exacerbate SARS pathogenesis by modulating intrinsic functions of monocyte-derived macrophages and dendritic cells. J Virol. 8 2009, vol. 83(7), p. 3039-48. Epub Nov. 14, 2008.
Yousefzadeh-Chabok et al., "The Relationship Between Serum Levels of Interleukins 6, 8, 10 and Clinical Outcome in Patients with Severe Traumatic Brain Injury." Arch Trauma Res, 2015, vol. 4(1), p. e18357.
Zhao, Q., Dual targeting of CCR2 and CCR5: therapeutic potential for immunologic and cardiovascular diseases. J Leukoc Biol, 2010, vol. 88, Issue 1, p. 41-55.
Zhou et al., CCR5 is a suppressor for cortical plasticity and hippocampal learning and memory. Elife. 2016;5. Epub Dec. 21, 2016.
U.S. Appl. No. 17/701,974, filed Mar. 23, 2022, Ruff, Michael R.
U.S. Appl. No. 17/816,448, filed Aug. 1, 2022, Ruff, Michael R.
U.S. Appl. No. 17/869,925, filed Jul. 21, 2022, Ruff, Michael R.
Bongiovanni et al., Mutli-chemokine receptor antagonist RAP-103 inhibits opioid-derived respiratory depression, reduces opioid reinforcement and physical dependence, and noramlizes opioid-induced dysregulation of mseolimbic chemokine receptors in rates, Drug Alcohol Depend., 2022, vol. 238, p. 1-31.
International Search Report and Written Opinion for PCT/US2024/014413, mailed Aug. 23, 2024.
International Search Report and Written Opinion for PCT/US2024/030461, mailed Oct. 11, 2024.
Cataldo et al., The bivalent ligand MCC22 potently attenuates hyperalgesia in a mouse model of cisplatin-evoked neuropathic pain without tolerance or reward, Neuropharmacology, v158, Apr. 7, 2019, p. 1-28.
Chapa-Oliver et al., Capsaicin: From Plants to a Cancer-Suppressing Agent, Molecules, Jul. 27, 2016, v21(8), p. 1-14.
Jiang et al., Chemokines in chronic pain: cellular and molecular mechanisms and therapeutic potential, Pharmacology & Therapeutics, May 22, 2020, v212, p. 1-25.
Pevida et al., The chemokine CCL5 induces CCR1-mediated hyperalgesia in mice inoculated with NCTC 2472 tumoral cells, Neuroscience, Dec. 4, 2013, v259, p. 113-125.
Donaghy et al., The clinical characteristics of dementia with Lewy bodies and a consideration of prodromal diagnosis, Alzheimer's Research & Therapy, 2014, vol. 6, No. 46, p. 1-12.
Silva et al., Cofilin pathology is a new player on α-synuclein-induced spine impairment in modles of hippocampal synucleinopathy, bioRxiv, Feb. 2, 2021, p. 1-24.
Yan et al., Cofilin 1 promotes the aggregation and cell-to-cell transmission of asynuclein in Parkinson's disease, Biochemical & Biophysical Research Commun, 2020, vol. 529, p. 1053-1060.
Chen et al., Rapid heterologous desensitization of antinociceptive activity between mu or delta opioid receptors and chemokine receptors in rats. Drug Alcohol Depend, 2007, vol. 88, No. 1, p. 36-41.
Li et al., Advances in the use of opioids in treating neuropathic cancer pain, Ann Palliat Med, 2012, vol. 1, No. 1, p. 53-57.
Majchrzak et al., The newest cathinone derivatives as designer drugs: an analytical and toxicological review, Forensic Toxicol, 2018, vol. 36, p. 33-50.
Patil et al., Opioid use in the management of diabetic peripheral neuropathy (DPN) in a large commercially insured population. Clin J Pain, 2015, vol. 31, No. 5, p. 414-24.
Szabo et al., Heterologous desensitization of opioid receptors by chemokines inhibits chemotaxis and enhances the perception of pain. Proc Natl Acad Sci USA, 2002, vol. 99, No. 16, p. 10276-81.
US Food and Drug Administration. FDA's Efforts to Address the Misuse and Abuse of Opioids. Feb. 6, 2013, downloaded Feb. 19, 2025; URL: https://www.fda.gov/drugs/information-drug-class/fdas-efforts-address-misuse-and-abuse-opioids.
CDC Overdose Prevention. Understanding the opioid overdose epidemic. Nov. 1, 2024, downloaded Feb. 19, 25; URL: https://www.cdc.gov/overdose-prevention/about/understanding-the-opioid-overdose-epidemic.html.
Stern et al. Drug Delivery: Oral Delivery of Peptides by Petelligence Technology. Drug Development and Delivery. Accessed online at https://drug-dev.com/oral-delivery-of-peptides-by-peptelligence-technology/ on Aug. 5, 2019, 10 pages. (Year: 2013).*

(56) References Cited

OTHER PUBLICATIONS

Thermo. Technical Information. "N-Terminal Acetylation and C-Terminal Amidation of Peptides". 2004, 2 pages. (Year: 2004).*

* cited by examiner

FIG. 3A CCL2
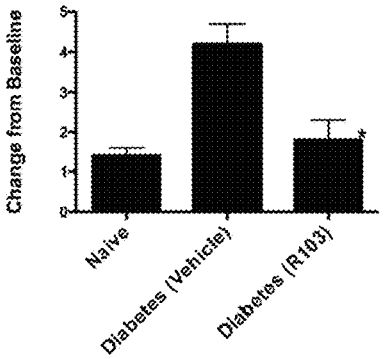
FIG. 3B CCL3
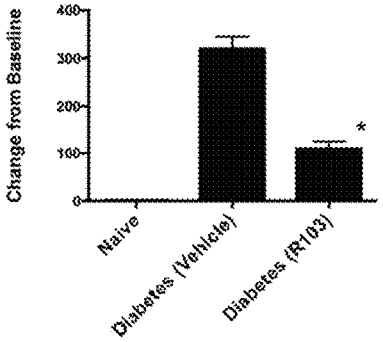
FIG. 3C CCR2
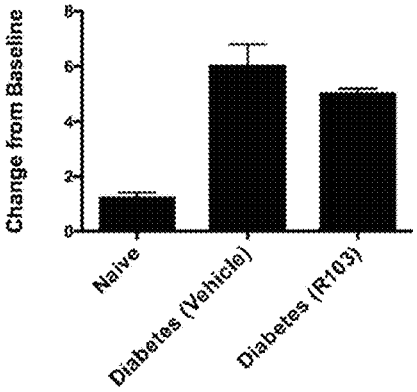
FIG. 3D CCR5
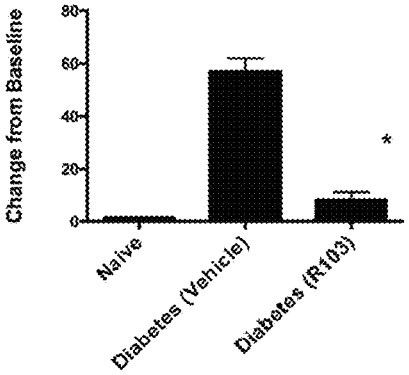
FIG. 3E IL1β
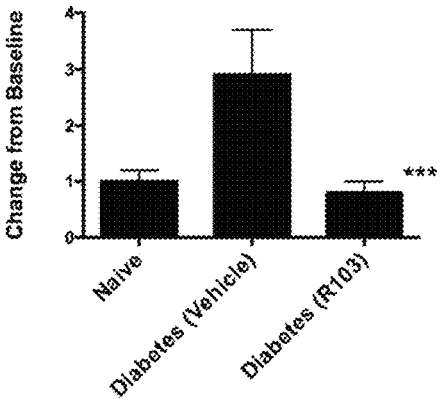
FIG. 3F TNFα
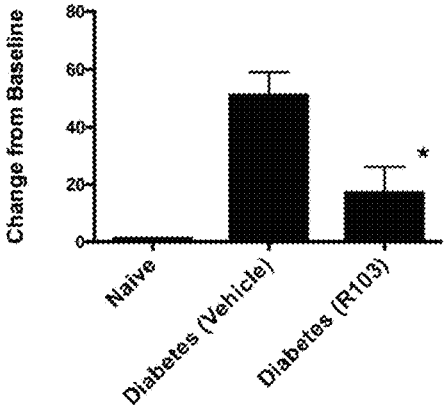

USE OF AN ALL-D-PENTAPEPTIDE CHEMOKINE ANTAGONIST TO REDUCE OPIOID DOSE IN A PERSON WITH PAIN

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

*CROSS-REFERENCE TO RELATED APPLICATIONS*

*This application is a reissue application of U.S. application Ser. No. 16/177,344, filed Oct. 31, 2018, now U.S. Pat. No. 10,624,945, issued Apr. 21, 2020, which claims the benefit of U.S. Provisional Application No. 62/579,545, filed Oct. 31, 2017, and is co-pending with reissue applications, application Ser. No. 17/701,974, filed Mar. 23, 2022, application Ser. No. 17/869,925, filed Jul. 21, 2022, and application Ser. No. 19/213,362, filed May 20, 2025, the disclosures of which are incorporated herein by reference in their entirety.*

BACKGROUND

The opioid epidemic is one of the most urgent health emergencies in our country today. Drug overdose is now the leading cause of death for Americans under 50. In 2017, the number of Americans who will die from drug overdose will be roughly the same as the number of Americans who died in the Vietnam, Iraq, and Afghanistan wars combined. Families are at risk due to the parents' addiction. Hundreds of millions of opioid painkillers are given out each year in the U.S. Medically sanctioned opioid prescriptions, such as in post-surgical pain, are often a gateway to addiction. Reduced opioid need would reduce addiction risks.

Severe pain, especially chronic pain, is frequently accompanied by inflammation. Although the most potent and effective drugs are the opioid analgesics, they are accompanied by a number of serious adverse effects, and they are not very effective in approximately half of the cases of chronic pain.

Chemokines desensitize opiate receptors and thereby enhance the perception of pain (Szabo, 2002, Chen, 2007). These findings provide a possible explanation for why opioids are relatively ineffective in inflammatory pain. Chemokines are released during inflammation, and they block the signaling of opioid receptors by a process of heterologous desensitization. From the data above, the hypothesis was formulated that a chemokine receptor antagonist (CRA), given with a suboptimal dose of morphine, will restore opioid analgesic efficacy by blocking the cognate chemokine ligand from binding to its receptor and desensitizing the opioid receptor.

Because opioids are used in the management of diabetic neuropathic pain (Patil, 2015). we determined the efficacy of a small peptide chemokine receptor antagonist RAP-103 (all-D-TTNYT) to block pain in a model of diabetic neuropathy.

Painful diabetic neuropathy (PDN) is a common complication of diabetes which adversely affects patients' daily life and represents a major public health problem. Although this painful signal is believed to originate in the peripheral nervous system, the precise cellular mechanisms of chronic pain associated with PDN remain poorly understood. Inspired by the critical contribution of inflammation in injury models of neuropathic pain, here we reasoned that if inflammation is also engaged in the pathogenesis of diabetic neuropathic pain, then 1) infiltration of immune cells in damaged nerves and/or activation of spinal microglia should coincide with the development of pain; 2) inhibiting inflammatory response in the peripheral and/or the central nervous system should reduce chronic pain. To test the hypothesis, we first used behavioral and molecular/cellular approaches to explore chronic pain development and inflammatory reaction in Streptozotocin (STZ) induced diabetic rats. Our results showed that following the induction of diabetes, rats exhibited persistent mechanical and cold allodynia (up to five months post-induction). The levels of inflammatory molecules, including cytokines, IL1β, TNFα; chemokines CCL2, CCL3; and chemokines receptors CCR2 and CCR5 were dramatically increased in sciatic nerves and RAP-103 lowered them (FIG. 3). Microglia in the spinal cord dorsal horns became activated with hypertrophic morphology and an increase in microglial cell number. CCL2 and CCL3 are two chemokines well known in mediating immune cell trafficking and immune response in the context of neuropathic pain. Oral administration of RAP-103, a CCR2/CCR5 dual receptor antagonist for 7 days inhibited PDN associated inflammation by reducing significantly all examined inflammatory mediators. The effect of RAP-103 is more pronounced at peripheral nerves.

BRIEF DESCRIPTION OF THE FIGURES

FIGS. 3A-F. RAP103 (0.5 mg/kg, for 7 days, p.o.) significantly inhibited inflammation in the sciatic nerves of STZ rats FIG. 4. RAP103 potentiates morphine analgesia in an animal model of post-surgical pain.

Figure 1A:
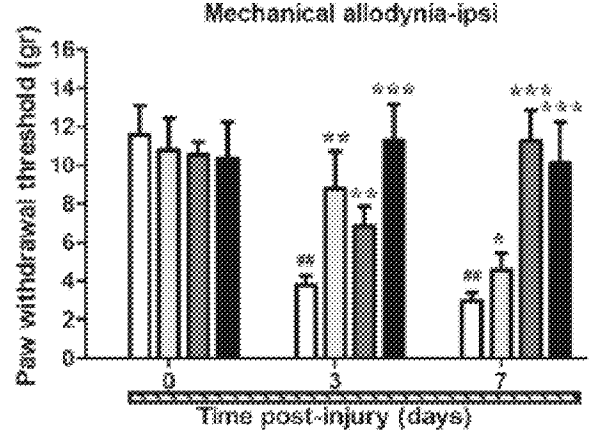
FIGS. 1A-B. RAP103 reversed mechanical allodynia in rats with neuropathic pain.
Figure 1B:
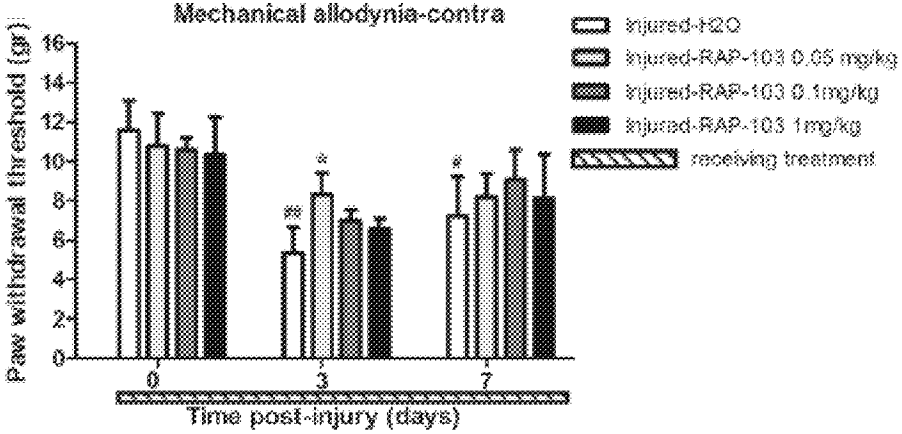
Figure 2A:
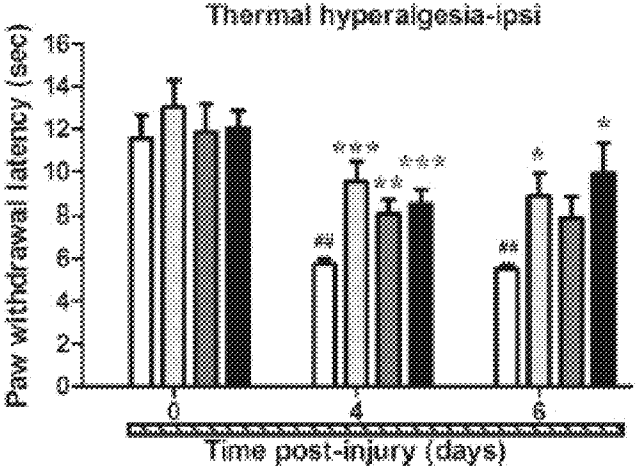
FIGS. 2A-B. RAP103 reversed cold allodynia in rats with neuropathic pain.
Figure 2B:
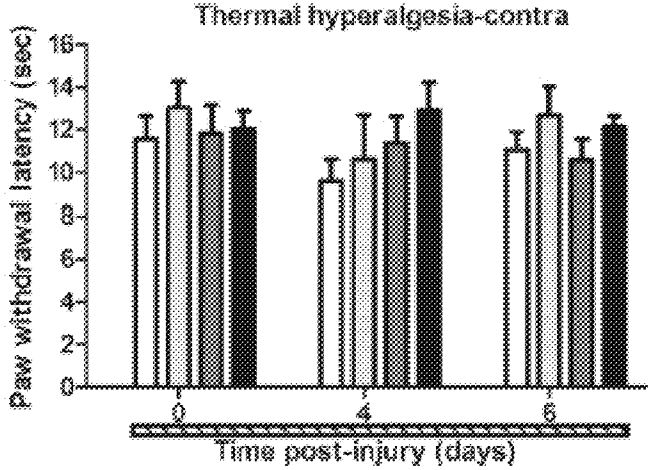

The treatment with RAP-103 (also referred to as R103) (0.5.-0.02 mg/Kg b.w., daily, for 7 days, resulted in a complete reversal of established hypersensitivity in STZ rats. The results suggest that functional antagonism of multiple chemokine receptors and innate immune receptors may be treatments and medicines for pain and inflammation. In view of the results showing that chemokines reduce opioid efficacy, these results suggest that administration of a chemokine receptor antagonist, like R103 (all-D-TTNYT), or related all-D-pentapeptides of the list below, will reduce pain by any cause, but especially inflammatory pain, to include back pain, post-surgical pain, neuropathic pain, cancer pain, pain from injury or trauma etc., and can reduce the amount or duration of opioid use in a person in need of pain control. The effective human doses suggested by these animal studies would be 0.01 to 2 mg/Kg/day. The peptides may be dosed as an oral pill, suspension, liquid, or by IV and subcutaneous injections to achieve pain control with decreased concomitant opioid use. Some examples of other useful CRA antagonists that can reduce opioid dose or use are Maraviroc (a CCR5 antagonist) or AMD3100 (a CXCR4 antagonist).

Materials and Methods

Induction and assessment of diabetes in rats Rats were fasted overnight and received a single intraperitoneal injection of streptozotocin (60 mg/kg, Sigma-Aldrich) in citrate buffer (pH 4.5) to induce type I diabetes. The induction of diabetes was confirmed 72 h after streptozotocin injection by measurement of blood glucose levels using Contour® blood glucose diagnostic kit (Bayer HealthCare, Canada). Body weight and blood glucose levels were measured before and 3 days after streptozotocin injection, once a week for three weeks after diabetes induction. Only rats having blood glucose concentration consistently higher than 300 mg/dl were used for the present study.

Drug Preparations:

The drug was prepared by dissolving 5 mg RAP103 in 50 ml autoclaved $H_2O$ at room temperature, which made up an initial concentration at 0.1 mg/ml. This source drug solution was prepared freshly for each experiment and it was kept for 8 days (duration of one experiment) at room temperature. Appropriate concentration for each dose was adjusted accordingly.

Treatment Paradigms

To investigate whether R103 (all-D-TTNYT), a drug which acts directly on CCR5 and CCR3 chemokine receptors can reverse already established neuropathic hypersensitivity in diabetic rats, autoclaved water or R103 (0.004, 0.02, 0.1 or 0.5 mg/kg b.w.) was administered daily by oral gavage to rats who exhibited stable mechanical and cold allodynia. The treatment lasted for 8 days (n=5 for $H_2O$ and n=7 for RAP-103/each dose).

Assessment of Pain Sensitivity

Tactile Allodynia

Mechanical sensitivity was assessed using calibrated von Frey hairs as described by Chaplan et al (1994). Animals were placed in Plexiglas boxes on an elevated metal mesh floor and allowed 60 min for habituation before testing. A series of von Frey filaments with logarithmically incrementing stiffness (Stoelting) was applied perpendicular to the mid-plantar region of the hind paw. The 50% paw withdrawal threshold was determined using Dixon's up-down method as previously described (Dixon, 1980). Withdrawal thresholds of both paws were averaged as one single value per animal.

Cold Allodynia

The same apparatus (Plexiglas cylinder resting on a mesh floor) as the one described above for the von Frey test was used. Rats were allowed adapting to the testing environment for at least 10 min. Then, a drop (50 ℓ) of acetone was applied with a glass syringe fitted with a blunted needle at the center of the plantar face of a hind paw. Acetone was applied alternately twice to each hind paw, with 5 min between each successive application. Responses were monitored during 1 min after acetone application and were graded according to a 4-point scale, as previously described by Flatters and Bennett (2004): 0, no response; 1, quick withdrawal, flick or stamp of the paw; 2, prolonged withdrawal or repeated flicking of the paw; 3, repeated flicking of the paw with persistent licking directed at the ventral side of the paw. Cumulative scores were then obtained by summing the four scores for each rat, the minimum score being 0 (no response to any of the four trials) and the maximum possible score being 12 (repeated flicking and licking of paws on each of the four trials).

Rats were habituated to the testing environment daily for at least two days before the experiments started. All animals were assessed for mechanical allodynia and cold allodynia of both hind paws before (behavioral baseline values before STZ injection) and once a week after diabetes induction until they exhibited stable hypersensitive states (before RAP103 treatment), where the treatment with RAP103 started. Assessment on the effects of RAP103 on mechanical and cold allodynia was performed between 2-4 hours following the drug administration.

Data Analysis

All data were presented as means±SEM. Statistical analysis was performed by two-way ANOVA followed by Bonferroni post-tests. The criterion for statistical significance was $P<0.05$.

Use of R103 to Reduce the Need for Opioids in the Treatment of Pain

Animals:

Male, Sprague-Dawley rats (210-250 g) were purchased from Taconic Biosciences and acclimated in the animal house for a week before initiation of experiments. At the beginning of testing, 2 days prior to surgery, rats were placed into individual transparent cubicles with a wire mesh floor for an hour a day, to acclimate them to the testing chambers.

Surgery:

On the day of surgery, rats were acclimated for 30 min in the chambers, and then their individual baseline values for mechanical allodynia were assessed. Paw withdrawal thresholds were measured using a series of von Frey filaments (North Coast Medical, Inc., Gilroy, Calif.), with gradually increasing logarithmic bending forces (equivalent to 2, 4, 6, 8, 10, 15, 26, and 60 g force). The filaments were applied to the plantar side of each hind paw in an ascending matter. Each filament was tested five consecutive times a few seconds apart. A positive response was defined as quick withdrawal or paw flinching after the application of a filament. Surgery was performed under isoflurane anesthesia (4% isoflurane for induction and 2.5% isoflurane for maintenance of anesthesia) using aseptic conditions. A 1 cm longitudinal incision (starting 0.5 cm from proximal edge of the heel and extending toward the toes) was made with a scalpel through skin and the fascia of the plantar side of the left hind paw. The plantaris muscle was exposed, elevated and incised longitudinally. Following bleeding control with gentle pressure, the skin was closed with two single interrupted sutures using 5-0 nylon. Animals were brought back to their individual chambers for mechanical allodynia testing. For kinetic assessment of pain, the time of surgery completion was designated as time 0. Paw withdrawal thresholds were recorded by a person blinded to the treatments at time points of 15, 30, 45, 60, 120, 240, and 360 min on the day of surgery, as well as 24, 48, and 72 h after surgery.

Treatment:

The compound, RAP-103, a CCR2/CCR5/CCR8 antagonist was tested for analgesic capacity. RAP-103 was supplied as a powder, and was reconstituted in sterile, pyrogen-free water. Solutions were prepared and kept frozen until use. On the day of the experiment, solutions were thawed and kept on ice until they were injected into rats. Rats were injected i.p., 25 min post-surgery. Control animals received water (vehicle). Morphine sulfate was dissolved in pyrogen-free saline and injected s.c. in the dorsal flank at 25 min post-surgery.

Co-Administration of RAP-103 with Morphine

Figure 4:
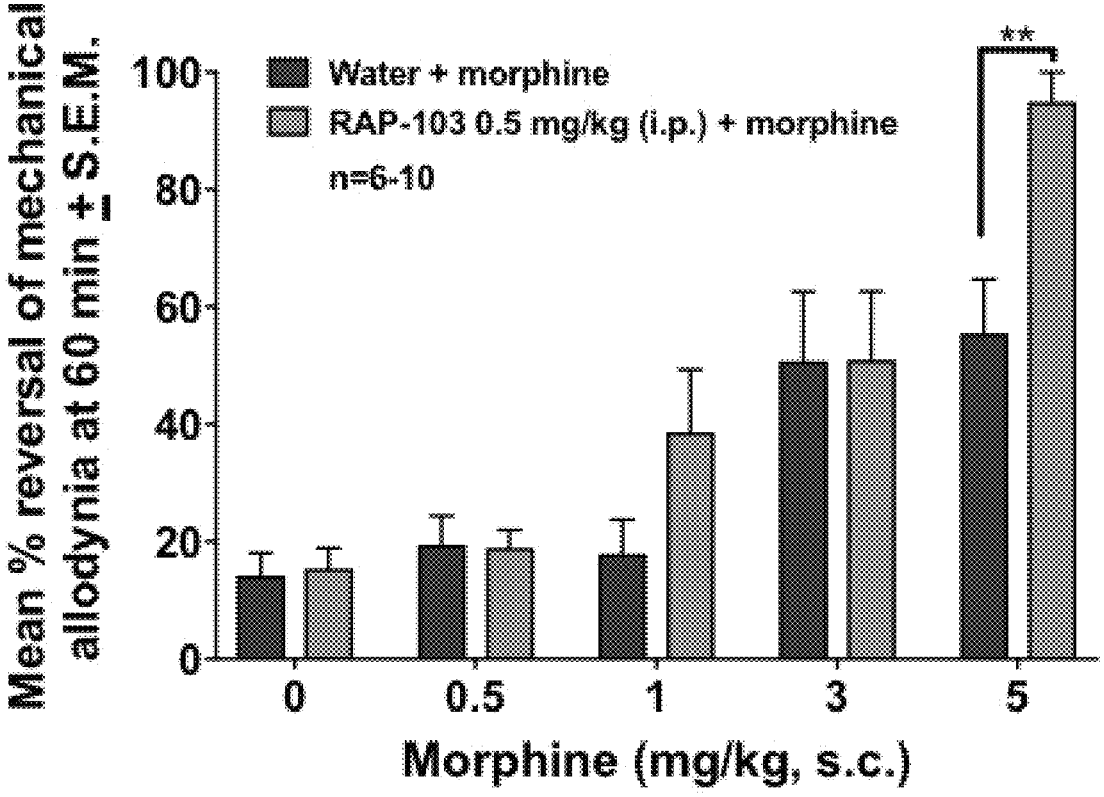

In this experiment, RAP-103 at a single dose, 0.5 mg/kg, was combined with morphine (0.5 to 5.0 mg/kg) and the percent reversal of mechanical allodynia was compared to that of morphine alone at the different doses. The range of doses for morphine were previously established in our laboratory in this assay. FIG. 4 shows that when 5.0 mg/kg of morphine was compared to the same dose of morphine plus 0.5 mg/kg of RAP-103, statistically significantly greater analgesia was observed in animals receiving the combination treatment, than in rats receiving morphine alone.

Dose Response Curves of Morphine Alone Compared to Morphine Plus RAP-103

A comparison of morphine alone at different doses with morphine plus RAP-103 was tested in the incisional pain assay. Percent reversal of mechanical allodynia was calculated using data from t=60 min. % reversal=[(60 min threshold−predose threshold)/(baseline threshold−predose threshold)]×100. Data were analyzed by two-way ANOVA followed by Sidak's multiple comparison test, **$p<0.01$.

Figure 5:
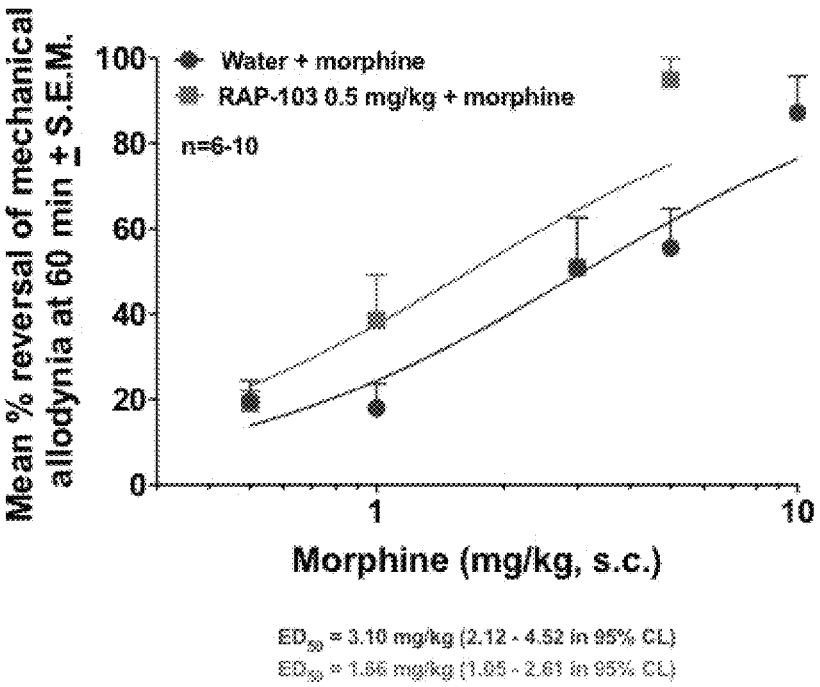
FIG. 5. Dose response curves of morphine alone compared to morphine plus RAP-103.

In FIG. 5 dose response curves are shown for morphine alone and for morphine plus RAP-103 (0.5 mg/kg) for ability to reverse mechanical allodynia, a measure of pain sensitivity. The $ED_{50}$ values were calculated from the graphic dose-response curves. As shown, the $ED_{50}$ for morphine was shifted to the left by about 2-fold by the addition of RAP-103. The ability of RAP-103 to potentiate opioid efficacy suggests further uses of RAP-103, and the related peptides of the invention, to be novel treatments for addictions in general, and opioid use disorders in particular.

Szabo, I., et al., Heterologous desensitization of opioid receptors by chemokines inhibits chemotaxis and enhances the perception of pain. Proc Natl Acad Sci USA, 2002. 99(16): p. 10276-81.

Chen, X., et al., Rapid heterologous desensitization of antinociceptive activity between mu or delta opioid receptors and chemokine receptors in rats. Drug Alcohol Depend, 2007. 88(1): p. 36-41.

Patil, P. R., et al., Opioid use in the management of diabetic peripheral neuropathy (DPN) in a large commercially insured population. Clin J Pain, 2015. 31(5): p. 414-24.

SEQUENCE LISTING

```
<160> NUMBER OF SEQ ID NOS: 13

<210> SEQ ID NO 1
<211> LENGTH: 5
<212> TYPE: PRT
<213> ORGANISM: Human immunodeficiency virus

<400> SEQUENCE: 1

Thr Thr Asn Tyr Thr
1               5


<210> SEQ ID NO 2
<211> LENGTH: 5
<212> TYPE: PRT
<213> ORGANISM: Human immunodeficiency virus

<400> SEQUENCE: 2

Ser Ser Thr Tyr Arg
1               5


<210> SEQ ID NO 3
<211> LENGTH: 5
<212> TYPE: PRT
<213> ORGANISM: Human immunodeficiency virus

<400> SEQUENCE: 3

Ser Thr Asn Tyr Thr
1               5


<210> SEQ ID NO 4
<211> LENGTH: 5
<212> TYPE: PRT
<213> ORGANISM: Human immunodeficiency virus

<400> SEQUENCE: 4

Thr Thr Ser Tyr Thr
1               5


<210> SEQ ID NO 5
<211> LENGTH: 5
<212> TYPE: PRT
<213> ORGANISM: Human immunodeficiency virus

<400> SEQUENCE: 5

Asn Thr Ser Tyr Gly
1               5
```

<210> SEQ ID NO 6
<211> LENGTH: 5
<212> TYPE: PRT
<213> ORGANISM: Human immunodeficiency virus

<400> SEQUENCE: 6

Glu Thr Trp Tyr Ser
1 5

<210> SEQ ID NO 7
<211> LENGTH: 5
<212> TYPE: PRT
<213> ORGANISM: Human immunodeficiency virus

<400> SEQUENCE: 7

Asn Thr Ser Tyr Arg
1 5

<210> SEQ ID NO 8
<211> LENGTH: 5
<212> TYPE: PRT
<213> ORGANISM: Human immunodeficiency virus

<400> SEQUENCE: 8

Ile Asn Asn Tyr Thr
1 5

<210> SEQ ID NO 9
<211> LENGTH: 5
<212> TYPE: PRT
<213> ORGANISM: Human immunodeficiency virus

<400> SEQUENCE: 9

Ile Asp Asn Tyr Thr
1 5

<210> SEQ ID NO 10
<211> LENGTH: 5
<212> TYPE: PRT
<213> ORGANISM: Human immunodeficiency virus

<400> SEQUENCE: 10

Thr Asp Asn Tyr Thr
1 5

<210> SEQ ID NO 11
<211> LENGTH: 5
<212> TYPE: PRT
<213> ORGANISM: Human immunodeficiency virus

<400> SEQUENCE: 11

Thr Asp Ser Tyr Ser
1 5

<210> SEQ ID NO 12
<211> LENGTH: 5
<212> TYPE: PRT
<213> ORGANISM: Human immunodeficiency virus

<400> SEQUENCE: 12

Thr Asn Ser Tyr Arg
1 5

<210> SEQ ID NO 13

-continued

```
<211> LENGTH: 5
<212> TYPE: PRT
<213> ORGANISM: Human immunodeficiency virus

<400> SEQUENCE: 13

Asn Thr Arg Tyr Arg
1               5
```

What is claimed is:

1. A method of reducing [the] *an* effective amount or duration of *an* opioid in a patient using said [opioids] *opioid* to manage pain comprising [the steps of]:

[preparing] *administering to the patient a therapeutically effective dose of* a chemokine receptor antagonist pharmaceutical composition comprising an all-D peptide and a pharmaceutically acceptable carrier, [said] *wherein the all-D* peptide comprises five contiguous amino acids and is at most 8 amino acid residues in length, having the general structure: A-B-C-D-E in which:

A is Ser, Thr, Asn, Glu, *or* Ile,

B is Ser, Thr, Asp, *or* Asn,

C is Thr, Ser, Asn, Arg, *or* Trp,

D is Tyr, and

E is Thr, Ser, Arg, *or* Gly,

*wherein in the all-D peptide,* all *stereoisomeric* amino acids [being] *are in* the D stereoisomeric configuration and, [administering said composition to the patient in a therapeutically effective dose,]

wherein [said] *the administering of the chemokine receptor antagonist pharmaceutical* composition acts to manage pain and reduce the effective amount or duration of opioid use in the patient.

2. The method [as defined in] *of* claim 1 wherein [said] *the all*-D peptide is TTNYT (SEQ ID NO: 1).

3. The method [as defined in] *of* claim 1 wherein the *all*-D peptide has a sequence selected from the group consisting of:

```
                                (SEQ ID NO: 1)
Thr Thr Asn Tyr Thr,

                                (SEQ ID NO: 2)
Ser Ser Thr Tyr Arg,

                                (SEQ ID NO: 3)
Ser Thr Asn Tyr Thr,

                                (SEQ ID NO: 4)
Thr Thr Ser Tyr Thr,

                                (SEQ ID NO: 5)
Asn Thr Ser Tyr Gly,

                                (SEQ ID NO: 6)
Glu Thr Trp Tyr Ser

                                (SEQ ID NO: 7)
Asn Thr Ser Tyr Arg

                                (SEQ ID NO: 8)
Ile Asn Asn Tyr Thr,
```

-continued

```
                                (SEQ ID NO: 9)
Ile Asp Asn Tyr Thr

                                (SEQ ID NO: 10)
Thr Asp Asn Tyr Thr

                                (SEQ ID NO: 11)
Thr Asp Ser Tyr Ser

                                (SEQ ID NO: 12)
Thr Asn Ser Tyr Arg,
and

                                (SEQ ID NO: 13)
Asn Thr Arg Tyr Arg.
```

4. The method [as defined in] *of* claim 1 wherein E is esterified, glycosylated, or amidated to enhance tissue distribution.

5. The method [as defined in] *of* claim 1 wherein [said] *the chemokine receptor antagonist pharmaceutical* composition is [used as an oral] *in the form of a* pill [having] *comprising* between 0.5 to 100 mgs of the *all-D* peptide, *and wherein the administering is oral administering.*

6. The method [as defined in] *of* claim 1 wherein [said] *the chemokine receptor antagonist pharmaceutical* composition is [used as an oral] *in the form of a* pill [having] *comprising* between 0.1 to 500 mgs of the *all-D* peptide *and wherein the administering is oral administering.*

7. The method [as defined in] *of* claim 1 wherein [said chemokine receptor antagonist] *the administering of the chemokine receptor antagonist pharmaceutical composition* reduces the effective amount of opioid use by the patient.

[8. The method as defined in claim 1 wherein said chemokine receptor antagonist is Dala1-peptide T-amide (DAPTA).]

[9. The method as defined in claim 1 wherein said chemokine receptor antagonist is Dala1-peptide T-amide (DAPTA) and is used to reduce the effective amount of opioid used by need for opioid used by the patient.]

10. [A method of pain treatment as defined in] *The method of* claim 1 wherein [said] *the* chemokine receptor antagonist *pharmaceutical composition* is administered as a pill or liquid.

*11. A method of reducing the effective amount or duration of an opioid in a patient using said opioids to manage pain comprising: administering to the patient a therapeutically effective dose of a pharmaceutical composition comprising Dala1-peptide T-amide (DAPTA) and a pharmaceutically acceptable carrier, wherein the DAPTA is at most 8 amino acid residues in length and wherein the administering of the pharmaceutical composition acts to manage pain and reduce the effective amount or duration of opioid use in the patient.*

* * * * *